US012691139B2

(12) United States Patent
 Pizzocaro

(10) Patent No.: US 12,691,139 B2
(45) Date of Patent: Jul. 28, 2026

(54) ANTIVIRAL AGENTS FOR PREVENTION OR TREATMENT OF PATHOLOGIES CAUSED BY ALPHA- AND/OR BETA-CORONAVIRUSES

(71) Applicant: Fidia Farmaceutici S.p.A., Abano Terme (IT)

(72) Inventor: Carlo Pizzocaro, Abano Terme (IT)

(73) Assignee: FIDIA FARMACEUTICI S.p.A., Abano Terme (IT)

( * ) Notice: Subject to any disclaimer, the term of this patent is extended or adjusted under 35 U.S.C. 154(b) by 469 days.

(21) Appl. No.: 18/268,371

(22) PCT Filed: Dec. 22, 2021

(86) PCT No.: PCT/IB2021/062161
§ 371 (c)(1),
(2) Date: Jun. 20, 2023

(87) PCT Pub. No.: WO2022/137147
PCT Pub. Date: Jun. 30, 2022

(65) Prior Publication Data
US 2024/0299442 A1     Sep. 12, 2024

(30) Foreign Application Priority Data
Dec. 23, 2020     (IT) ........................ 102020000032243

(51) Int. Cl.
| | |
|---|---|
| *A61K 31/737* | (2006.01) |
| *A61K 31/728* | (2006.01) |
| *A61K 47/10* | (2017.01) |
| *A61K 47/32* | (2006.01) |
| *A61P 31/14* | (2006.01) |

(52) U.S. Cl.
CPC .......... *A61K 31/737* (2013.01); *A61K 31/728* (2013.01); *A61K 47/10* (2013.01); *A61K 47/32* (2013.01); *A61P 31/14* (2018.01)

(58) Field of Classification Search
CPC ..... A61K 31/737; A61K 31/728; A61K 31/14
See application file for complete search history.

(56) References Cited

U.S. PATENT DOCUMENTS

| | | | | |
|---|---|---|---|---|
| 2005/0004071 A1* | 1/2005 | Comper | ............... | A61K 31/737 |
| | | | | 514/54 |
| 2005/0009782 A1* | 1/2005 | Comper | ............... | A61K 31/728 |
| | | | | 514/54 |
| 2010/0080823 A1* | 4/2010 | O'Hagan | ............... | A61K 39/00 |
| | | | | 424/209.1 |
| 2012/0101059 A1* | 4/2012 | Galesso | .................... | A61P 9/10 |
| | | | | 514/54 |
| 2013/0209531 A1* | 8/2013 | Prestwich | .............. | A61K 8/735 |
| | | | | 424/56 |
| 2016/0175241 A1 | 6/2016 | Scarci et al. | | |
| 2017/0274006 A1* | 9/2017 | Saaid | .................. | A61K 31/728 |

FOREIGN PATENT DOCUMENTS

| | | |
|---|---|---|
| EP | 3 103 459 A2 | 12/2016 |
| EP | 3 103 459 A3 | 1/2017 |

OTHER PUBLICATIONS

De Francesco et al., "COVID-19 and Diabetes: The Importance of Controlling RAGE" Frontiers in Endocrinology vol. 11 article 525, pp. 1-6, doi: 10.3389/fendo.2020.00526 (Year: 2020).*
Chen et al., "Application prospect of polysaccharides in the development of anti-novel coronavirus drugs and vaccines", International Journal of Biological Macromolecules, 2020, vol. 164, pp. 331-343.
International Search Report, issued in PCT/IB2021/062161, dated Mar. 18, 2022.
Siddharta et al., "Virucidal Activity of World Health Organization-Recommended Formulations Against Enveloped Viruses, Including Zika, Ebola, and Emerging Coronaviruses", The Journal of Infectious Diseases, Mar. 15, 2017, vol. 215, pp. 902-906.
Written Opinion of the International Searching Authority, issued in PCT/IB2021/062161, dated Mar. 18, 2022.

* cited by examiner

*Primary Examiner* — Andrea Olson
(74) *Attorney, Agent, or Firm* — Birch, Stewart, Kolasch & Birch, LLP

(57) ABSTRACT

Ester and sulfated derivatives of hyaluronic acid are described for use in the prevention and treatment of the initial stage of SARS-CoV-2 disease.

12 Claims, No Drawings

ANTIVIRAL AGENTS FOR PREVENTION OR TREATMENT OF PATHOLOGIES CAUSED BY ALPHA- AND/OR BETA-CORONAVIRUSES

OBJECT OF THE INVENTION

The present invention relates to new antiviral agents.

Early in January 2020, the world health authorities identified the virus responsible for the epidemic that broke out in Wuhan (CN) which then (in March 2020) turned into a pandemic: it is a betacoronavirus called SARS-CoV-2, part of the family of Coronaviridae (single-stranded RNA-virus). This virus has the typical external corona that characterizes coronaviruses, consisting of Spike glycoproteins, a glycoprotein system that represents the key for allowing entry of the virus into the host cell: for this purpose, the virus uses two host membrane receptors, the first is the heparan sulfate proteoglycan, a low-affinity receptor essential for the adhesion of the virus to the host cell membrane as it collects and converges the virus to the second receptor, the functional ACE2 receptor which allows the effective entry of the virus into the cell (Hao Wei et al., doi.org/10.1101/2020.05.17.100537; Zhou Peng et al., Nature, 2020, 579, 270-273). The ACE2 receptor is part of the renin/angiotensin system for blood-pressure control, it is present in the epithelial cells of the nose, pharynx, larynx, trachea, bronchi, but especially in the pneumocytes and enterocytes. The main target organs of SARS-CoV-2 are therefore the lungs and intestines. The virus is transmitted via droplets in the air and by contact.

Before this discovery, only six coronaviruses were known (including alpha- and beta-coronaviruses) capable of infecting humans, and more specifically HCoV-229E, HCoV-OC43. HCoV-NL63, HCoV-HKU1, responsible for a considerable percentage of cases of the common cold associated with mild symptoms. SARS-CoV and MERS-CoV are instead two coronaviruses related to a much more serious clinical presentation even with lethal outcomes. SARS-CoV-2 is therefore the seventh virus in the same family that involves humans. To date, many characteristics of the virus are still unclear and, although its ability to be transmitted from human to human has been ascertained, uncertainties still remain about the exact mode of transmission and its pathogenicity (Hasoksuz M. et al., Turk J Med Sci, 2020, 549-556).

SARS-CoV-2 virus infection can lead to the development of an important disease called COVID-19 (CoronaVirus Disease 2019), patients experience flu-like symptoms such as fever, fatigue, dry cough and difficulty in breathing. In the most serious cases, often found in subjects already burdened by previous illnesses, pneumonia, acute renal failure develops, up to the patient's death. The lethality rate varies from country to country, but depends above all on the type of person infected, therefore on the age, type and number of previous diseases and, of course, on access to hospitalization.

As of July 2020 there was still no effective treatment for the cure of this disease: in milder cases, the US Centers for Disease Control and Prevention (CDC) recommended relieving symptoms by regularly taking anti-flu drugs such as NSAIDs and antipyretics, in cases with particular symptoms, treatment with steroids, antivirals, hyperimmune serum or synthetic antibodies (still in the testing phase) was indicated, whereas in the more serious cases it was often necessary to support the vital functions, by treatments such as artificial ventilation and ECMO (Yan-Rong Guo et al., *Military Medical Research*, 2020, 7-11).

To date, the medical clinic has tested numerous drugs belonging to pharmacological classes also very different from each other, such as classic steroidal anti-inflammatory drugs (Bentelan), inhibitory antibodies of the cytokine cascade (tocilizumab and sarilumab), protease inhibitors (Ritonavir), antimalarials (chloroquine), nucleotide analogues (Remdesivir), synthetic nucleosides (ribavirin) and also anti-protozoal (nitazoxamide), with initially encouraging but then often contradictory results, however indicated in the treatment of COVID-19 disease when the SARS-CoV-2 coronavirus has already severely compromised the patient's health, often with complications such as pneumonia.

There are no known drugs, on the other hand, indicated as treatment for the initial stage of the SARS-CoV-2 pathology, therefore for the first stage of the infection when the symptoms are still mild with symptoms such as fever, fatigue, dry cough and/or dyspnoea, but unfortunately it is not possible to predict its evolution, and what is more, there are no known drugs or devices indicated for preventive purposes for preventing the adhesion of the virus to its receptors and therefore blocking its entry into the host cells.

The present invention relates to ester and sulfated derivatives of hyaluronic acid (HA) for use in the prevention and treatment of the initial stage of the SARS-CoV-2 pathology, as the Applicant has surprisingly found and demonstrated the specific antiviral/virucidal properties vs this virus of the derivatives object of the invention.

HA is a hetero-polysaccharide composed of alternating residues of D-glucuronic acid and N-acetyl-D-glucosamine. It is a linear chain polymer with a molecular weight (MW) ranging from 50,000 to $13\times10^6$ Da depending on the source from which it is obtained and the preparation methods used. It is present in the pericellular gels, in the fundamental substance of the connective tissue of vertebrate organisms (of which it is one of the main components), in the synovial fluid of the joints, in the vitreous humor and in the umbilical cord. HA therefore plays an important role in the biological organism, especially as a mechanical support for the cells of many tissues such as the skin, tendons, muscles and cartilage, exerting functions such as tissue hydration and joint lubrication; furthermore, through its CD44 membrane receptor, HA modulates many and different processes related to cell physiology and biology such as, for example, proliferation, migration, cell differentiation and angiogenesis.

For many years, scientific and patent literature has been studying and describing sulfated hyaluronic acid (HAS), a synthetic polysaccharide prepared from hyaluronic acid suitably sulfated at its hydroxyl groups as described by the state of the art (EP0940410, EP3377536), to which initially mainly anticoagulant effects were attributed. This polysaccharide can also be obtained by de-acetylation of HA with subsequent sulfation of glucosamine (therefore defined as HA-NS), this however is a different molecule with different functions (EP0971961). Over time, multiple experiments with HAS have led to the discovery of its new uses, such as its use as an anti-inflammatory agent in diseases such as ARDS, joint rheumatism, rheumatoid arthritis and dermatitis (EP754460 and EP1385492), its use as a regulatory agent of the cytokine activity (WO2010130466) and, finally, also its use as an antiviral agent, as, in EP3103459, a specific antiviral activity is claimed against the strains of Herpes virus, HIV, Cytomegalovirus and vesicular stomatitis virus (VSV).

Another derivative of HA, object of the invention, is the ester between its carboxyl groups with alcohols of the aliphatic, arylaliphatic, cycloaliphatic, aromatic, cyclic and heterocyclic (Hyaff®) series, with an esterification percentage that can vary depending on the type and the length of the alcohol used (EP216453); hyaluronic acid esters are among the HA derivatives that are particularly important in the formation process of new engineered tissues, benzyl esters with an esterification percentage ranging from 75 to 100% are particularly interesting from this point of view. The use of these ester derivatives is in fact known for the formation of fibers which, processed in non-woven fabric, form a three-dimensional matrix that can be used both in the orthopedic and in the dermatological field (EP618817). Numerous scientific experiments have amply demonstrated how Hyaff is a completely biocompatible biodegradable polymer (Campoccia D. et al., *Biomaterials,* 1998, 19: 2101-2127), capable of inducing and promoting the proliferation and differentiation of various cell types attached to this polymer, for the in vitro production of new artificial tissues (Brun P. et al., *J Biomed Mater Res,* 1999, 46: 337-346; Aigner J. et al., *J Biomed Mater Res.* 1998, 42: 172-181).

DETAILED DESCRIPTION OF THE INVENTION

The present invention relates to ester and sulfated derivatives of hyaluronic acid selected from sulfated hyaluronic acid with an average sulfation degree per disaccharide unit equal to 3 (HAS3) and benzyl ester of hyaluronic acid (HA) with an average carboxyl esterification percentage of 50% (Hyaff11p50) for use in the prevention and treatment of the pathology caused by alpha- and/or betacoronavirus, preferably the SARS-CoV-2 virus.

The present invention further relates to topical pharmaceutical compositions comprising said HAS3 or Hyaff11p50, preferably in the pharmaceutical form of nasal or oropharyngeal sprays, or in the form of nebulizable solutions such as aerosols, in association with suitable excipients (such as, for example, stabilizers, solvents, gelling polymers or preservatives, as known to the person skilled in the field), for use in the prevention and treatment of the pathology caused by alpha- and/or betacoronavirus, in particular the SARS-CoV-2 virus, and preferably in the treatment of the initial stage of the disease caused by the SARS-CoV-2 virus.

The HA used in the present invention for the preparation of HAS3 and Hyaff11p50 can derive from any source as known to the skilled person in the field, for example from rooster-comb extraction (EP138572, EP3491027), from the fermentation of Streptococcus Equi or *Zooepidemicus* (EP716688, EP3491027. EP3655138), or biosynthetically (from *Bacillus,* EP2614088), and can have a weight average molecular weight (MW) ranging from 150 to 250 kDa.

It should be pointed out that weight average molecular weight refers to the weight average MW calculated with the "intrinsic viscosity" method (Terbojevich et al., *Carbohydr Res.* 1986, 363-377).

HAS3 is prepared according to what is known to the skilled person in the field (for example EP0940410), preferably as described in EP2429533 and EP3377536; the sulfation of HA takes place exclusively at the level of its hydroxyl groups to obtain an average sulfation degree per disaccharide unit equal to 3 (i.e. with an average sulfation degree equal to 3 sulfate groups per disaccharide unit: HAS3), this process therefore does not involve the glucosamine of HA.

The invention also relates to topical pharmaceutical compositions comprising said HAS3 for the use described above, preferably in the pharmaceutical form of nasal or oropharyngeal sprays, or as nebulizable solutions such as aerosols, optionally in association with suitable excipients, wherein this derivative is present in a concentration ranging from 0.1 to 10% by weight with respect to the total weight of the composition (w/w), and preferably in a concentration ranging from 2% w/w to 5% w/w, conveyed with saline (0.9% NaCl) or PBS, in the form of a nebulizable solution.

The benzyl ester of HA is prepared according to what is known to the skilled person in the field (for example EP216453); the esterification of HA exclusively involves its carboxyl groups and leads to the formation of Hyaff 11p50, i.e. the benzyl ester of HA whose carboxyl groups are esterified in an average percentage of 50%.

The invention further relates to topical pharmaceutical compositions of Hyaff 11p50 for the use described above, preferably in the pharmaceutical form of nasal and oropharyngeal sprays, in association with suitable excipients, stabilizers or preservatives, wherein this derivative is present in a concentration ranging from 0.1 to 1% by weight with respect to the total weight of the composition (w/w), and preferably in a concentration equal to 0.2% w/w, associated with a gelling agent such as Carbomer (INCI name of Carbopol®: synthesis polymer of polyacrylic acid). Carbomer/Carbopol 934 or Carbomer/Carbopol 5984EP is preferable (identical synthesis polymers of polyacrylic acid prepared in different solvents), preferably present in a concentration that varies within the range of 0.5%-1.5% w/w and even more preferably in a concentration equal to 0.9% w/w, and propylene glycol as wetting agent/solvent, preferably present in a concentration that varies within the range of 5%-15% w/w and even more preferably in a concentration equal to 10% w/w, and also possibly associated with preservative agents. pH regulators, and any other excipient deemed appropriate by the skilled person in the field.

The preferred topical pharmaceutical composition of Hyaff11p50 is indicated hereunder, in the form of a nasal/oropharyngeal spray (A), for use in the prevention and treatment of the pathology caused by alpha- and/or betacoronavirus, in particular the SARS-CoV-2 virus, and preferably in the treatment of the initial stage of the pathology caused by the SARS-CoV-2 virus, whose composition is as follows:

| Farmaceutical composition A: | | |
|---|---|---|
| Component | Quantity in grams | Function |
| Hyaff11p50 | 0.2 | Active agent |
| Carbomer/Carbopol 934 or Carbomer/Carbopol 5984EP | 0.9 | Gelling agent |
| Propylene glycol | 10 | Wetting agent |
| Methyl p-hydroxybenzoate | 0.1 | Preservative agent |
| Propyl p-hydroxybenzoate | 0.05 | Preservative agent |
| Sodium dehydroacetate | 0.1 | Preservative agent |
| Peppermint oil | 0.005 | Flavouring agent |
| Sodium hydroxide | q.s.* to pH = 5.5-6.5 | PH regulator |
| Ethoxylated Hydrogenated Castor Oil 40 | 0.025 | Solubilizing agent |
| Purified water | q.s.* to 100 grams | Solvent |

*q.s.: quantum sufficit, as much as it is sufficient.

For purely descriptive and non-limiting purposes, some preparation examples are provided, together with the results obtained from the in vitro experimentation.

Example 1

Synthesis of Sulfated HA Starting from HA Having an Average MW of 200 KD, with an Average Sulfation Degree Equal to 3 Sulfate Groups Per Disaccharide Unit: HAS3

1.00 grams of HA sodium salt (200 KD) were suspended in 55 ml of dimethyl sulfoxide (DMSO), 0.8 ml of pure methanesulfonic acid were added to this suspension and the mixture was mixed for 24 hours at 25° C.; a clear and colourless solution was thus obtained (Absorbance at 600 nm=0.02 AU). 5.0 g of a pyridine sulfur trioxide complex (Pyridine $SO_3$) were added to this solution, under stirring for a further 24 hours at 25° C.

90 ml of ethanol were then added to the solution thus prepared, obtaining a brown-coloured rubbery precipitate which was separated by filtration, solubilized in 32 ml of water with the addition of 1.3 g of NaCl. 24 mL of DMSO were finally added and the pH was adjusted to 3.4 with 3 M NaOH. The derivative obtained was precipitated as a very fine powder by adding 90 ml of ethanol; it was then separated by filtration and washed 3 times with an ethanol/water solution (8/2). In order to eliminate the residual pyridine, the powder was washed 3 more times with an ethanol/0.1 M NaOH solution (8:2), 2 times with an ethanol/0.1 M HCl solution (8:2), 2 times with an ethanol/water solution (8:2) and, finally, 2 more times with pure ethanol. The yellowish-white powder thus obtained was dried in a vacuum pump at 40° C. for 24 hours. 1.70 g of HAS3 were obtained as a very fine white-yellowish powder, which correspond to a yield of 98% with a purity of 99.4%.

Example 2

Preparation of the Benzyl Ester of HA in which 50% of its Carboxyl Groups are Esterified with Benzyl Alcohol: Hyaff11p50

10.6 g of HA tetrabutylammonium salt (having an average MW of 200 KD), corresponding to 17 milliequivalents of monomer units, were solubilized in 530 ml of DMSO at 25° C. 7.8 milliequivalents of benzyl bromide were then added and the resulting solution was kept at 30° C. for 12 hours. A solution of 62 ml of water containing 9 g of sodium chloride was subsequently added, and the resulting mixture was slowly poured into 3,000 ml of acetone with constant stirring. The precipitate formed was filtered, washed three times with 500 ml of acetone/water 5:1, and finally dried under vacuum at 30° C. for 8 hours. The precipitation step was repeated; the precipitate was then washed twice with acetone/water 5:1, and then 3 times with acetone alone; it was finally dried under vacuum at 30° C. for 24 hours.

The quantitative determination of the ester groups of Hyaff11p50 was effected according to Cundiff and Markunas, *Anal Chem*, 1961, 33, 1028-1030.

Example 3

Evaluation of the Antiviral Action of HAS3

The activity of the sample tested was determined in vitro by evaluating its effective antiviral capacity against the BCoV virus (i.e. bovine coronavirus belonging to the species Betacoronavirus 1, strain S379 Riems) in PT cells (CCLV-RIE 11, bovine kidney cells) kept in culture with suitable mediums. BCoV is a recognized and valid betacoronavirus which is used and can be used in the experimentation and inactivation studies of MERS-CoV, SARS-CoV, and SARS-CoV-2 viruses (Siddharta et al., *The Journal of Infectious Diseases*, 2017, 15; 215 (6): 902-906). The experimental procedure was carried out according to the European legislation EN 14476: 2013+A2: 2019 which regulates the methods for determining the virucidal activity of antiseptic products usable in the medical field.

Before use, the BCoV virus was expanded (in terms of number of infecting viral particles) using PT cells incubated with this virus for 2-3 days at 37° C.; the cell preparation was then centrifuged and the supernatant (hereinafter defined as viral suspension) containing the above-mentioned virus was then collected. The viral titer was expressed as $TCID_{50}$/ml of viral suspension ($TCID_{50}$: the cytopathic infectious dose capable of infecting 50% of the inoculated cell units, therefore corresponds to the dilution of the viral suspension capable of inducing a cytopathic effect in 50% of the inoculated cells; $TCID_{50}$ was calculated using the Spearmar-Karber method (Kärber G., *Archiv f. experiment. Pathol. u. Pharmakol*, 1931, 162, 480-483; Spearman C I, *Br J Psychol*, 1908, 2: 227-242) after evaluating, under a microscope, the effective dose of virus capable of causing cytopathic effects on the treated cells). For this assay, the viral titer had to be at least $10^8$ $TCID_{50}$/ml of suspension.

For this test, different concentrations of HAS3 were used, previously tested for ensuring the lack of cytotoxicity. HAS3 was prepared according to Example 1 and tested at a concentration of 1. 4 mg/ml in PBS
2. 2 mg/ml in PBS
3. 0.2 mg/ml in PBS.

The PT cells were seeded in 96-well plates and tested when reaching their confluence.

Experimental Model: Acute Evaluation 1 ml of the viral suspension was diluted with 9 ml of the above samples, for a contact time of 30 minutes at 20° C.; these preparations were subsequently diluted 1:10 to scale to obtain serial solutions always diluted 1:10 with culture medium.

0.1 ml of each serial solution was then put in contact with the cells contained in the wells of the 96-well plates (6 wells for each dilution, 1 plate for each sample). After 60 minutes of exposure of the cells to the above solutions at 37° C., all the solutions tested were removed by suction and an equal quantity of culture medium was added (in substitution).

The negative control is given by 6 wells per plate that are not treated (the respective cells must therefore always be alive); the positive control for comparison with the plates treated with the above serial solutions (for all dilutions) on the other hand, consists of 1 plate inoculated with the same viral dilutions of the above-mentioned solutions but without the samples tested, for evaluating the antiviral capacity of the samples analyzed.

All the cells treated were observed under a microscope after 48 hours in order to evaluate the viability % and any viral pathological effects, the $TCID_{50}$ value was then calculated for the samples and for the positive control.

The evaluation of the antiviral efficacy of the samples tested was determined by calculating the log reduction of the viral titer (expressed as log $TCID_{50}$) of the cells treated at the various concentrations/dilutions of the samples tested, vs the viral titer (log $TCID_{50}$) of the positive control, then subtracting the $TCID_{50}$ log value of the samples tested from the $TCID_{50}$ log value of the positive control.

Experimental Model: Chronic Evaluation

The same experimental model used for the acute evaluation was effected with the following modifications:

after 60 minutes of exposure of the cells to the above serial solutions at 37° C. a further 0.1 ml of culture medium were added to these cells in the solutions tested. After 48 hours of treatment, the cultures were observed under a microscope for the evaluation of the % survival and the cellular pathogenicity caused by the virus or inhibited by the sample tested, always vs the positive control. After this analysis, the respective $TCID_{50}$ was calculated for all samples.

Results

The reduction in the viral titer determined for each sample in both models used, is summarized hereunder in Table 1-2:

TABLE 1

| Log reduction of $TCID_{50}$ determined by HAS3 vs the positive control; acute treatment after 48 hours | | |
|---|---|---|
| Virus | HAS3 | HAS3 | HAS3 |
| BCoV | 4 mg/ml Log. Red. = 2.00 | 2 mg/ml Log. Red. = 2.00 | 0.2 mg/ml Log. Red. = 1.00 |

TABLE 2

| Log reduction of $TCID_{50}$ determined by HAS3 vs the positive control; chronic treatment after 48 hours | | |
|---|---|---|
| Virus | HAS3 | HAS3 | HAS3 |
| BCoV | 4 mg/ml Log. Red. = 1.00 | 2 mg/ml Log. Red. = 1.00 | 0.2 mg/ml Log. Red. = 1.00 |

The formula applied for converting these values into a % of reduction in the BCoV infectious capacity operated by the samples tested (*Log and Percent Reductions in Microbiology and Antimicrobial Testing*, Microchem Laboratory, Dec. 16, 2015) is the following:

$$P=(1-10^{-L})\times100$$

wherein P is the percentage of reduction in the viral load obtained

L is the log reduction (log $TCID_{50}$) of the viral load obtained for each sample in the two experimental models used, written above. Thus, by replacing L with the above values, the following are obtained:

for L=1, P=90% reduction for L=2, P=99% reduction.

HAS3 caused in both the acute and chronic models in which it was tested and for all the concentrations evaluated, a decrease in the viral load and therefore in the infectious capacity of the betacoronavirus ranging from 90% to 99%, demonstrating an efficient and effective antiviral property against this type of virus.

Example 4

Evaluation of the Antiviral Action of the Pharmaceutical Composition a Containing the Hyaff11p50 Derivative Hyaff11p50 was prepared as described in Example 2.

The antiviral activity of composition A was determined in vitro by evaluating its effective antiviral capacity vs the BCoV virus (i.e. bovine betacoronavirus belonging to the species Betacoronavirus 1, strain S379 Riems) in PT cells (CCLV-RIE 11), kept in culture with the appropriate media.

The experimentation was carried out completely analogously to that effected for HAS3 indicated above, in short, also in this case the BCoV virus, before use, was expanded using PT cells incubated with this virus for 2-3 days at 37° C.; the cell preparation was then centrifuged and the supernatant containing the above-mentioned virus collected. The viral titer was expressed as $TCID_{50}$/ml of viral suspension, wherein the $TCID_{50}$ was calculated using the above Spearmar-Karber method, after evaluating, under a microscope, the effective dose of virus capable of causing cytopathic effects on the cells treated. Also for this test the viral titer had to be at least $10^8$ $TCID_{50}$/ml of suspension.

For this test, 2 different dilutions of composition A were used, previously tested to ensure the lack of cytotoxicity:

1. composition A tested at a dilution of 66% in 0.9% NaCl 2. composition A tested at a dilution of 6.6% in 0.9% NaCl.

Experimental Model: Acute Evaluation

The two dilutions of composition A (above) were tested in the acute experimental model previously described for the HAS3 test.

Also in this case, the cells treated were observed under a microscope after 48 hours to assess the % of viability and any pathological effects, the viral activity was then determined by calculating the $TCID_{50}$ value. The evaluation of the antiviral efficacy of the two dilutions was determined by calculating the log reduction of the viral titer of the treated cells vs the viral titer (log $TCID_{50}$) of the positive control.

Experimental Model: Chronic Evaluation

The two dilutions of composition A were tested in the chronic experimental model previously described for the HAS3 test.

After 48 hours of treatment, the cultures were observed under a microscope for the evaluation of the % survival and the cellular pathogenicity caused by the virus or inhibited by the sample tested, again vs the positive control. After this analysis, the respective $TCID_{50}$ was calculated for all of the samples.

Results

For the 2 dilutions of composition A tested in both models used, the reduction in the viral titer expressed as a logarithmic value is summarized hereunder (in Tables 3-4):

TABLE 3

| Log reduction of $TCID_{50}$ determined by Composition A vs the positive control; acute treatment after 48 hours | | |
|---|---|---|
| Virus | Comp. A containing Hyaff11p50 | Comp. A containing Hyaff11p50 |
| BCoV | Dilution 66%<br>Log. Red. = 2.00 | Dilution 6.6%<br>Log. Red. = 1.00 |

TABLE 4

| Log reduction of $TCID_{50}$ determined by Composition A vs the positive control; chronic treatment after 48 hours | | |
|---|---|---|
| Virus | Comp. A containing Hyaff11p50 | Comp. A containing Hyaff11p50 |
| BCoV | Dilution 66%<br>Log. Red. = 1.00 | Dilution 6.6%<br>Log. Red. = 1.00 |

$$P=(1-10-L)\times100$$

By replacing L with the above value, the following are obtained:

for L=1, P=90% reduction for L=2, P=99% reduction.

In summary, HAS3 and the preferred pharmaceutical composition A containing Hyaff11p50, caused, in both the acute and chronic models, for all concentrations tested and for both dilutions evaluated, a radical decrease in the infectious dose $TCID_{50}$ i.e. of the infectious load/capacity of betacoronavirus, ranging from 90% to 99% thus demonstrating an effective and efficacious antiviral property against this type of virus.

Example 5

The Applicant carried out two further different experiments to test the antiviral action of HAS3 against the Human Rhinovirus virus (enterovirus of the Picornaviridae family that penetrates by air diffusion, becomes localized and multiplies in the nasal mucosa), and of the Simian virus (polyomavirus of the Polyomaviridae family, potential tumour virus).

For this purpose, the HR-37 rhinovirus tested in HELA cells (immortalized tumour cells), and the Simian virus SV40 in CV-1 cells (monkey kidney fibroblasts) were used; for both cases, the European legislation EN 14476: 2013+ A1: 2015 was followed, which regulates the methods for determining the virucidal activity of antiseptic products usable in the medical field.

For both the rhinovirus and the Simian virus, HAS3 did NOT produce any virucidal effect, consequently it did not demonstrate any antiviral power against the above-mentioned viruses.

In conclusion, with these experiments the Applicant demonstrated how both HAS3 and Hyaff1p50 (in association with Carbomer and propylene glycol), hereinafter for the sake of simplicity defined as "products", are capable of exerting a preventive action and curative antiviral treatment vs coronavirus pathology, as the acute cell experimentation effected after a first virus/product incubation clearly demonstrated how both of these products are capable of exerting a highly effective preventive virucidal/antiviral action, which is maintained over time as, after 48 hours of observation, the cells treated were found to be alive and at least 90% morphologically healthy with respect to the positive control;

the chronic cellular experimentation in which the coronavirus remains in contact with the cells treated continuously for 48 hours (always in the presence of the product), clearly demonstrated how both of these products are capable of exerting a highly effective curative antiviral action by blocking the replication of the residual virus in the culture medium, the cells treated were found to be alive and morphologically healthy at least 90% more with respect to the positive control;

the experimentation of HAS3 with enteroviruses and polyomaviruses did not produce any results proving that its virucidal/antiviral action is specific for the coronavirus and not applicable to other viral families, therefore not generically extensible to the whole viral world.

The invention claimed is:

1. A method of treating or preventing a pathology caused by alpha- and/or betacoronavirus, which comprises administering to a subject an ester and/or sulfated derivative of hyaluronic acid selected from sulfated hyaluronic acid with an average sulfation degree per disaccharide unit equal to 3 (HAS3) and benzyl ester of hyaluronic acid (HA) with an average carboxyl esterification percentage of 50%, wherein if the derivative of hyaluronic acid is the benzyl ester of HA with an average carboxyl esterification percentage of 50%, it is present within a concentration range of 0.1 to 1% by weight with respect to the total weight of the composition (w/w).

2. The method of claim 1, wherein the treating is in the initial stage of the pathology caused by SARS-CoV-2 virus.

3. The method of claim 1 wherein the ester and/or sulfated derivative of hyaluronic acid is in a pharmaceutical form of nasal, oropharyngeal spray, or nebulizable solution, associated with suitable excipients.

4. The method of claim 1, wherein the sulfated derivative of hyaluronic acid is in a pharmaceutical composition comprising HAS3 in a concentration range of 0.1 to 10% by weight with respect to the total weight of the composition (w/w), conveyed with NaCl 0.9% w/w or PBS as a nebulizable solution.

5. The method of claim 1, wherein the ester of hyaluronic acid is in a pharmaceutical composition comprising the benzyl ester of HA with an average carboxyl esterification percentage of 50% associated with a Carbomer/Carbopol excipient, and with propylene glycol, and optionally associated with further excipients.

6. The method of claim 5, wherein the Carbomer/Carbopol is present in a concentration varying within the range of 0.5%-1.5% w/w, and the propylene glycol is present in a concentration varying within the range of 5%-15% w/w, optionally associated with further excipients.

7. To The method of claim 5, wherein the Carbomer/Carbopol is present in a concentration equal to 0.9% w/w, and the propylene glycol is present in a concentration equal to 10% w/w.

8. The method of claim 1, wherein the ester of hyaluronic acid is in a pharmaceutical composition comprising the benzyl ester of HA with an average carboxyl esterification percentage of 50% in a concentration equal to 0.2% w/w, associated with the Carbomer/Carbopol excipient in a concentration equal to 0.9% w/w, with propylene glycol in a concentration equal to 10% w/w, and optionally associated with further excipients.

9. The method of claim 1, wherein the alpha- and/or betacoronavirus is a SARS-CoV-2 virus.

10. The method of claim 4, wherein the HAS3 is in a concentration range of 2% w/w to 5% by weight with respect to the total weight of the composition (w/w).

11. The method of claim 1, wherein the benzyl ester of HA with an average carboxyl esterification percentage of 50% is in a concentration of 0.2% by weight with respect to the total weight of the composition (w/w).

12. The method of claim 3, wherein the nebulizable solution is an aerosol.

\* \* \* \* \*